(12) United States Patent
Bachman et al.

(10) Patent No.: US 6,573,994 B2
(45) Date of Patent: Jun. 3, 2003

(54) OPTICAL METHOD TO MONITOR THE PROCESSING OF A STARCH-CONTAINING MATERIAL

(75) Inventors: Stephen E. Bachman, Amarillo, TX (US); Michael E. Hubbert, Taos, NM (US)

(73) Assignee: Ganado Research, L.L.C., Amarillo, TX (US)

( * ) Notice: Subject to any disclaimer, the term of this patent is extended or adjusted under 35 U.S.C. 154(b) by 0 days.

(21) Appl. No.: 09/785,119

(22) Filed: Feb. 16, 2001

(65) Prior Publication Data

US 2002/0154304 A1 Oct. 24, 2002

(51) Int. Cl.$^7$ .................................................. G01J 3/50
(52) U.S. Cl. ......................... 356/402; 356/407; 426/231
(58) Field of Search .............................. 356/402, 405, 356/406, 407, 425; 426/231, 233

(56) References Cited

U.S. PATENT DOCUMENTS

| | | | | |
|---|---|---|---|---|
| 4,707,138 A | * | 11/1987 | Coatney | ..................... 356/402 |
| 4,752,357 A | | 6/1988 | Baker | ......................... 162/263 |
| 5,350,593 A | * | 9/1994 | LaCourse et al. | ........... 426/253 |
| 5,391,384 A | * | 2/1995 | Mazza | ........................ 426/267 |
| 5,598,770 A | * | 2/1997 | Campbell et al. | ............. 99/487 |
| 5,740,079 A | | 4/1998 | Shigemori et al. | .......... 364/526 |
| 5,880,826 A | | 3/1999 | Jung et al. | ..................... 356/73 |

OTHER PUBLICATIONS

Minolta Co., Ltd, "Precise Color Communication—Color Control from Perception to Instrumentation", 1998, pp. 1–59.

* cited by examiner

Primary Examiner—F. L. Evans
(74) Attorney, Agent, or Firm—Dale P. Regelman

(57) ABSTRACT

An optical method to measure certain optical characteristics of starch-containing materials during and/or after processing. Certain properties of the processed starch-containing materials such as flake weight and starch availability can be accurately estimated from the measured optical characteristics.

10 Claims, 9 Drawing Sheets

OPTICAL METHOD TO MONITOR THE PROCESSING OF A STARCH-CONTAINING MATERIAL

FIELD OF THE INVENTION

The present invention relates to an optical method used to monitor the processing of a starch-containing material.

BACKGROUND OF THE INVENTION

Starch is a naturally-occurring material obtained from various plants such as potato, and tapioca, and cereal grains such as corn, rice, wheat, barley, and the like. Starches are polysaccharide compounds which on hydrolysis produce sugars. As used herein, starch can include a mixture of linear components generally referred to as amylose, and branched components generally referred to as amylopectin. Amylose generally has a molecular weight of several hundred thousand, while amylopectin generally has a molecular weight in the order of several million. The processing of starches containing 0 to 100% amylose or 0 to 100% amylopectin can be monitored using Applicants' optical method.

As used herein, starch should also be understood to include starches with a high amylopectin content sometimes called waxy starches, as well as chemically and physically modified starches, such as for example starches whose acid values have been reduced, starches in which the type and concentration of cations associated with the phosphate groups have been modified, ethoxylated starches, starch acetates, cationic starches, oxidated starches and cross-linked starches.

Starch forms a granule located with the endosperm of many plants, including the cereal grains. Cereal grains typically contain between about 60 weight percent to about 80 weight percent starch. Between about 0 weight percent and about 100 weight percent of this starch may exist in a crystalline state. Generally, between about 50 weight percent and about 100 weight percent of the starch in cereal grains exists in a crystalline domains.

When these starch granules are heated in the presence of water, the granules swell and the microstructure of the constituent starch becomes less crystalline. It is sometimes said that the starch is becoming destructurized. The water solubility of starch increases as the degree of crystallinity decreases. This process is sometimes referred to as starch gelatinization.

Most cereal grains are processed to expose and/or gelatinize starch. The microstructure of such gelatinized starch is less dense, and is more completely and more readily digested by mammals and bacteria. Processing methods include but are not limited to: grinding, dry rolling, steam rolling, pelleting, steam flaking, pressure flaking, popping, micronizing, exploding, extruding, roasting, high-moisture harvesting, and reconstitution.

Certain animals, including beef cattle, digest starch in various portions of the digestive tract. The degree of starch gelatinization in a cereal grain determines the amount of starch that can be digested in the rumen, or fore stomach, of a cow. Too little digestion of starch in the rumen results in inefficient use of the feed-stuff. On the other hand, too rapid digestion in the rumen may lead to digestive disorders. Therefore, the processing of starch-containing materials is monitored in order to ascertain, for example, the level of starch gelatinization A number of analytical protocols exist which are used to monitor the gelatinization of starch in a starch-containing foodstuff. These quality control protocols currently include, for example: flake weight measurement, microscopic examination (Schoch and Maywald, "Microscopic Examination of Modified Starches," Anal. Chem. 28:382, 1965), enzymatic analysis (Sung, An-Chein, "Enzymatic Evaluation of Changes in Processed Grains, Feedstuffs 19:22., 1960), and fermentation analyses (Croka and Wagner, "Micronized Sorghum Grain: Influence of In Vitro Digestibility, In Vitro Gas Production and Gelatinization, Journal of Animal Science, 40:931, 1975; Trei et. al., "Effect of Grain Processing on In Vitro Gas Production, J. Anim. Sci. 30:825., 1970).

These analytical procedures, however, suffer from certain disadvantages. For example, several of these techniques require pretreatment of the sample prior to analysis or are subject to operator bias. Microscopic examination requires subjective analysis by trained persons. Enzymatic analyses and fermentation analyses require use of laboratory equipment and trained personnel.

What is required is a reliable, easily performed, and low cost analytical method to estimate the degree of starch availability during or after the processing of starch-containing food-stuffs.

SUMMARY OF THE INVENTION

Applicants' invention includes a method to measure certain optical characteristics of a starch-containing material during and/or after processing in order to estimate the degree of starch availability. According to Applicants' method, samples of the starch-containing material are obtained during and/or after processing.

Light having a defined frequency and intensity is directed onto at least one surface of the test sample from one or more light sources. The light reflected from the sample is received through one or a plurality of light receivers. Certain optical characteristics of the reflected light are then measured. These measured optical characteristics include reflected surface color spectrum, reflected bulk material color spectrum, gloss translucency, fluorescence, and surface texture or a combination of the above. Sample attributes such as sample flake weight and starch availability can then be estimated by comparing the measured optical characteristics of the sample with known calibration curves.

When using wet processing methods, the optical properties measured relate to starch gelatinization. When using dry processing methods, the optical properties measured relate to starch exposure. In either event, the optical properties measured can be used to estimate the samples' flake weight and/or starch availability for wet processing or fineness of grind for dry processing.

In another embodiment, the calculated processing parameters, such as flake weight and/or starch availability, are displayed on a visual display device. In another embodiment, an oral representation of those calculated processing parameters is generated and announced.

BRIEF DESCRIPTION OF THE DRAWINGS

The invention will be better understood from a reading of the following detailed description taken in conjunction with the drawings in which like reference designators are used to designate like elements, and in which.

DETAILED DESCRIPTION OF THE PREFERRED EMBODIMENTS

Figure 1:
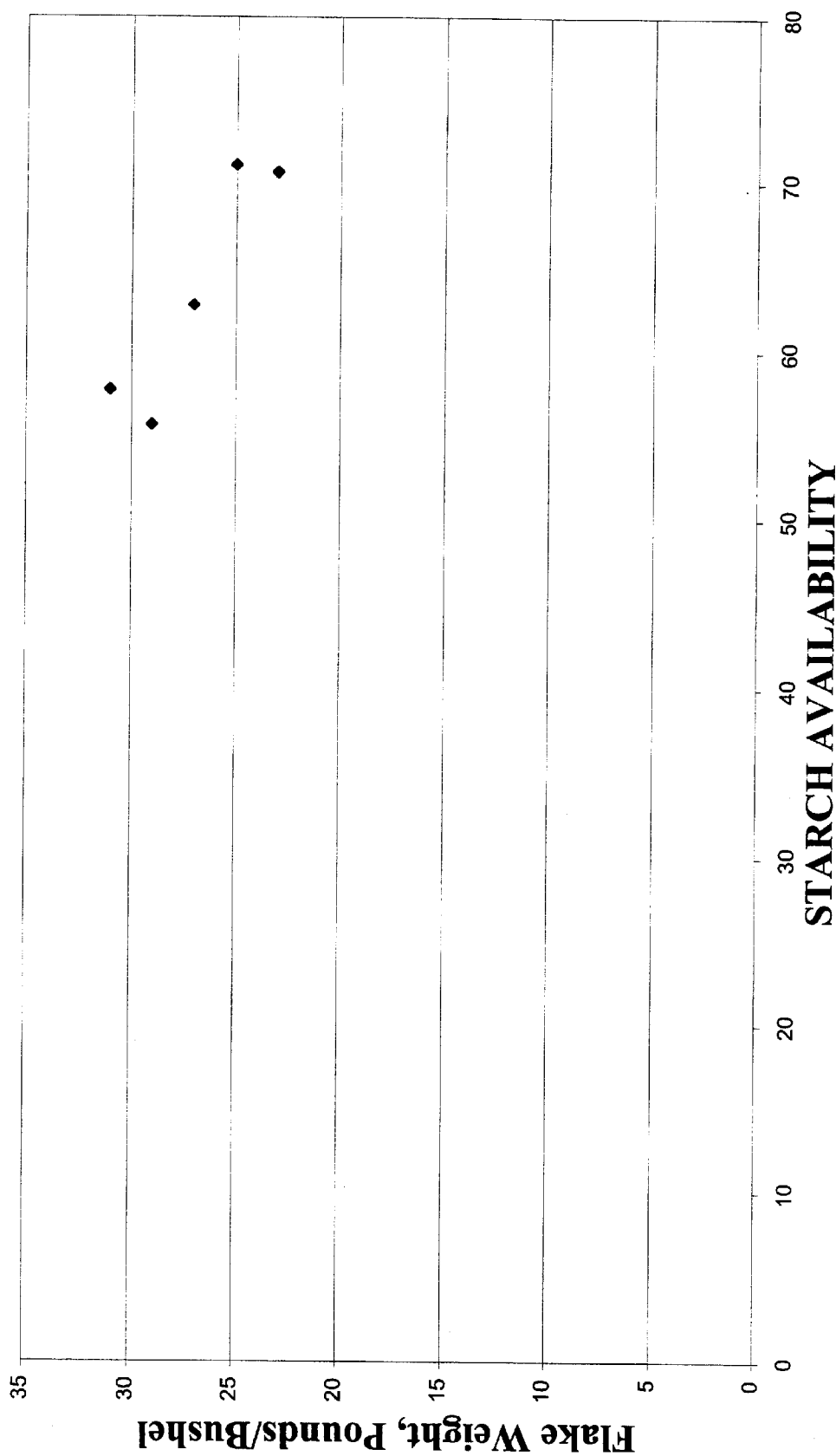
FIG. 1 graphically depicts flake weight and starch availability data obtained by laboratory analyses of five (5) test samples obtained at differing times during the steam processing of corn-based materials.

Applicants' have discovered that the degree to which starch in a starch-containing material has been gelatinized during wet processing influences certain optical characteristics of that starch-containing material. These optical characteristics include reflected surface color spectrum, reflected bulk material color spectrum, gloss translucency, fluorescence, and surface texture.

The color of an object determines the manner in which light is reflected from the surface of the object. When light is incident upon an object, the reflected light will vary in intensity and wavelength dependent upon the color of the surface of the object. Thus, a red object will reflect red light with a greater intensity than a blue or a green object, and correspondingly a green object will reflect green light with a greater intensity than a red or blue object.

One method of quantifying the color of an object is to illuminate it with broad band spectrum or "white" light, and measure the spectral properties of the reflected light over the entire visible spectrum and compare the reflected spectrum with the incident light spectrum. Such methods typically require use of a broad band spectrophotometer.

It is further known in the art that the color of an object can be represented by three values. It is important that the three values be orthogonal; i.e., any combination of two elements in the set cannot be included in the third element. One such set of orthogonal values includes the hue/lightness/saturation parameters.

In 1931 the Commission Internationale de l"Eclairage ("CIE") promulgated the Yxy color space based on the "tristimulus" values XYZ (the "Tristimulus Color Space"). A color space is a method for expressing the color of an object using some sort of notation, including numbers. The concept of XYZ tristimulus values is based upon the three-component theory of color vision which posits that the eye possess receptors for three primary colors (red, green, and blue).

In 1976, CIE defined what is known as the L*a*b* color space (the "CIE L*a*b* Color Space"). In this color space, L* indicates lightness, with a* and b* representing the chromaticity coordinates. L* values range from 0 to 100. A value near 0 represents a very dark color, and a value near 100 presents a very pale color.

The chromaticity coordinate a* and b* values range from −60 to +60. For example, +a* is in the red direction and −a* is in the green direction. On the other hand, +b* is in the yellow direction and −b* is in the blue direction.

One such method of quantifying the color of an object is to illuminate an object with broad band "white" light comprising virtually all visual frequencies, and to measure the intensity of the reflected light after it has been passed through a plurality of narrow band filters. Typically three filters (such as red, green and blue) are used to provide tristimulus light values representative of the color of the surface. Yet another method is to illuminate an object with three monochromatic light sources (such as red, green and blue) one at a time and then measure the intensity of the reflected light with a single light sensor. The three measurements are then converted to a tristimulus value representative of the color of the surface. Such color measurement techniques can be utilized to produce equivalent tristimulus values representative of the color of the surface.

Generally, it does not matter if a "white" light source is used with a plurality of color sensors (or a continuum in the case of a spectrophotometer), or if a plurality of colored light sources are utilized with a single light sensor. U.S. Pat. No. 5,880,826 teaches how to make and use an optical characteristic measuring system utilizing the above-discussed principles, and that patent is hereby incorporated by reference.

In one embodiment, Applicants' method uses a broadband light source, i.e. a "white" light source, in conjunction with a plurality of color sensors. In a separate embodiment, Applicants' method uses a plurality of colored light sources with a single light sensor.

The following example is presented to further illustrate to persons skilled in the art how to use Applicants' optical method, and to identify a presently preferred embodiment thereof. This example is not intended as a limitation, however, upon the scope of the invention, which is defined only by the appended claims.

EXAMPLE I

Corn was processed by steam flaking using a steam chest and corrugated rolls to gelatinize the starch component. Flaked corn samples were collected from below the rolls over a period of about 10 minutes. The flake weight in pounds per bushel of these samples was altered to change the degree of starch gelatinization. Samples with flake weights of 23, 25, 27, 29 and 31 pounds per bushel were split into two portions.

One portion of each sample was submitted to a commercial laboratory (SDK Laboratories, 1000 Corey Road, P.O. Box 886, Hutchinson, Kans. 67504-0886) for starch availability analyses using enzymatic methods. The greater the starch availability the greater the starch gelatinization. The starch availability data is presented in Table I, below.

TABLE I

| Flake Weight, Pounds/Bushel | Starch Availability |
|---|---|
| 23 | 70.6 |
| 25 | 71.0 |
| 27 | 62.7 |
| 29 | 55.6 |
| 31 | 57.7 |

Figure 2:
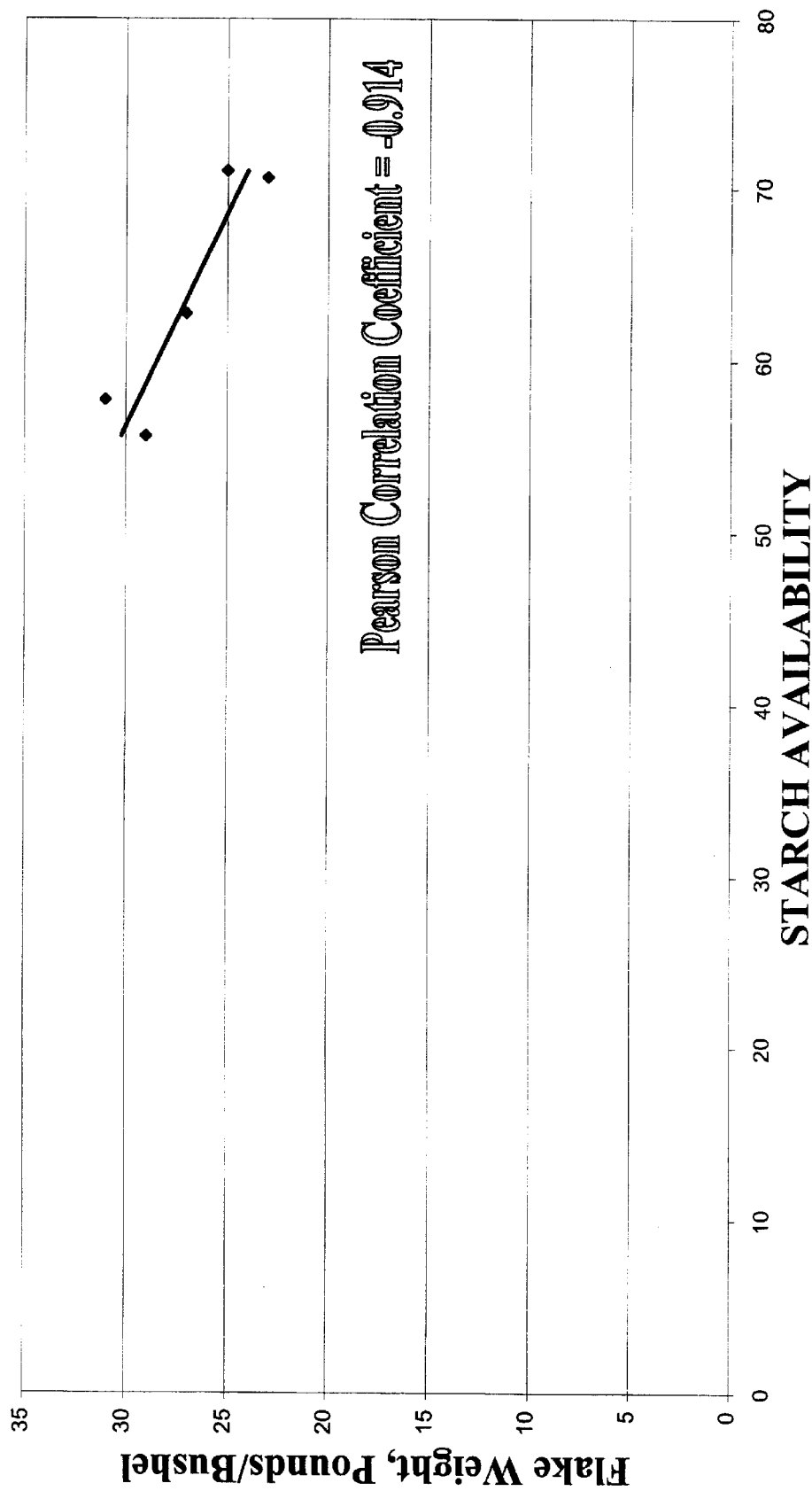
FIG. 2 shows the Pearson Correlation Coefficient for a best-fit straight line curve using the data points recited in FIG. 1.

Turning to FIG. 1, the measured starch availability for each flake weight sample is graphically depicted. An inverse relationship exists between starch availability and flake weight. Referring to FIG. 2, a linear regression analysis of the data recited in FIG. 1 shows a Pearson Correlation Coefficient of −0.914 and an $R^2$ value of 0.83. Thus, a roughly linear relationship exists between flake weight and starch availability. Thus, measured values for flake weight can be used to estimate the starch availability of a sample.

The second portions of each sample referred to above were analyzed using Applicants' optical method. In this embodiment, a Minolta Colorimeter Model CR-300 was used. The CIEL*a*b* color space is used to express the optical characteristics of the samples. Table II recites the observed CIEL*a*b* value for L* for each flake weight sample.

TABLE II

| Flake Weight, Pounds/Bushel | Lightness Value L* |
|---|---|
| 23 | 55.3 |
| 25 | 60.0 |
| 27 | 64.2 |
| 29 | 68.5 |
| 31 | 70.5 |

Figure 3:
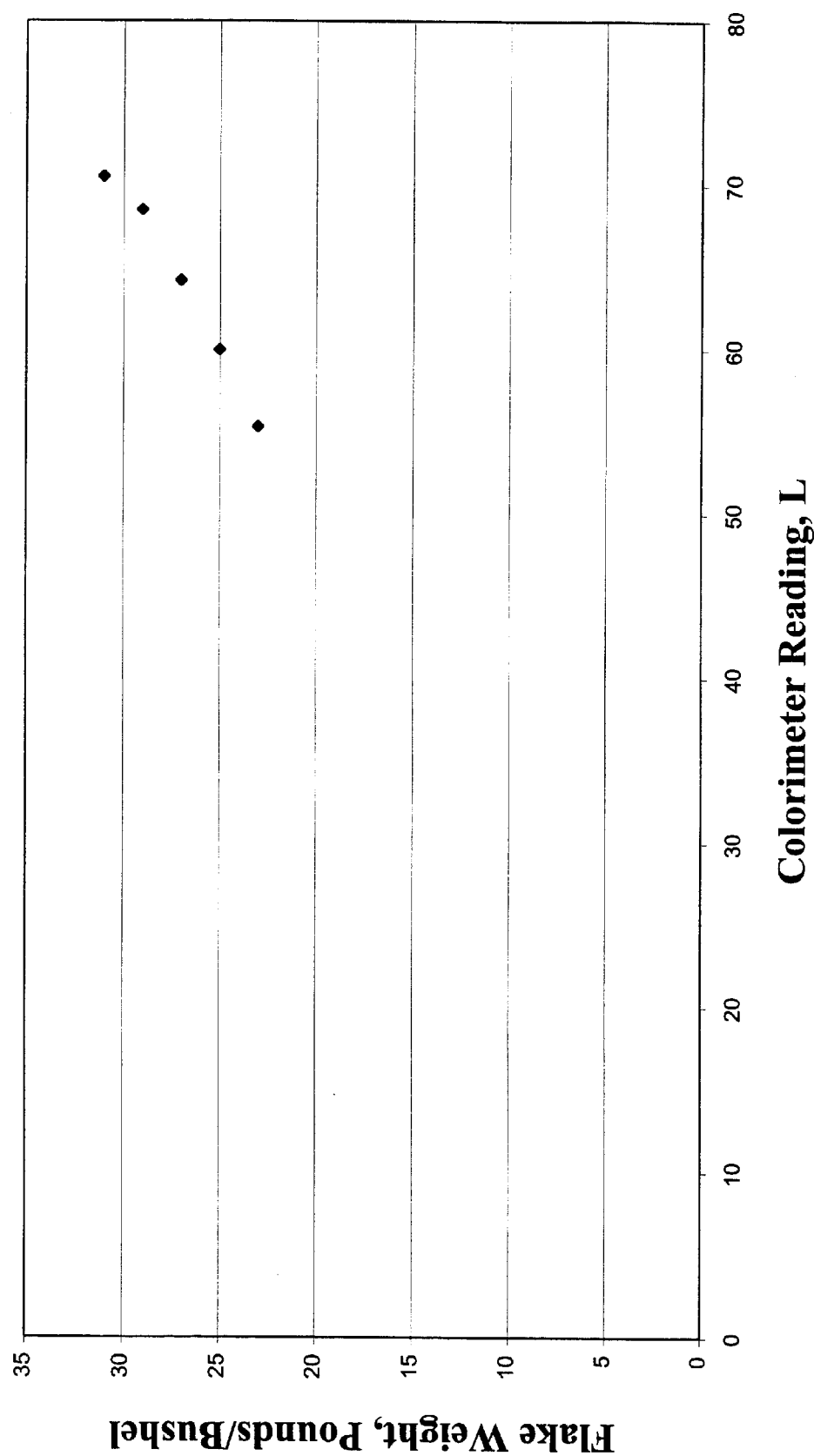
FIG. 3 graphically depicts the relationship between flake weight data obtained by mill personnel, and colorimetric data obtained using Applicants' optical method, of five (5) test samples obtained at differing times during the steam processing of corn-based materials.
Figure 4:
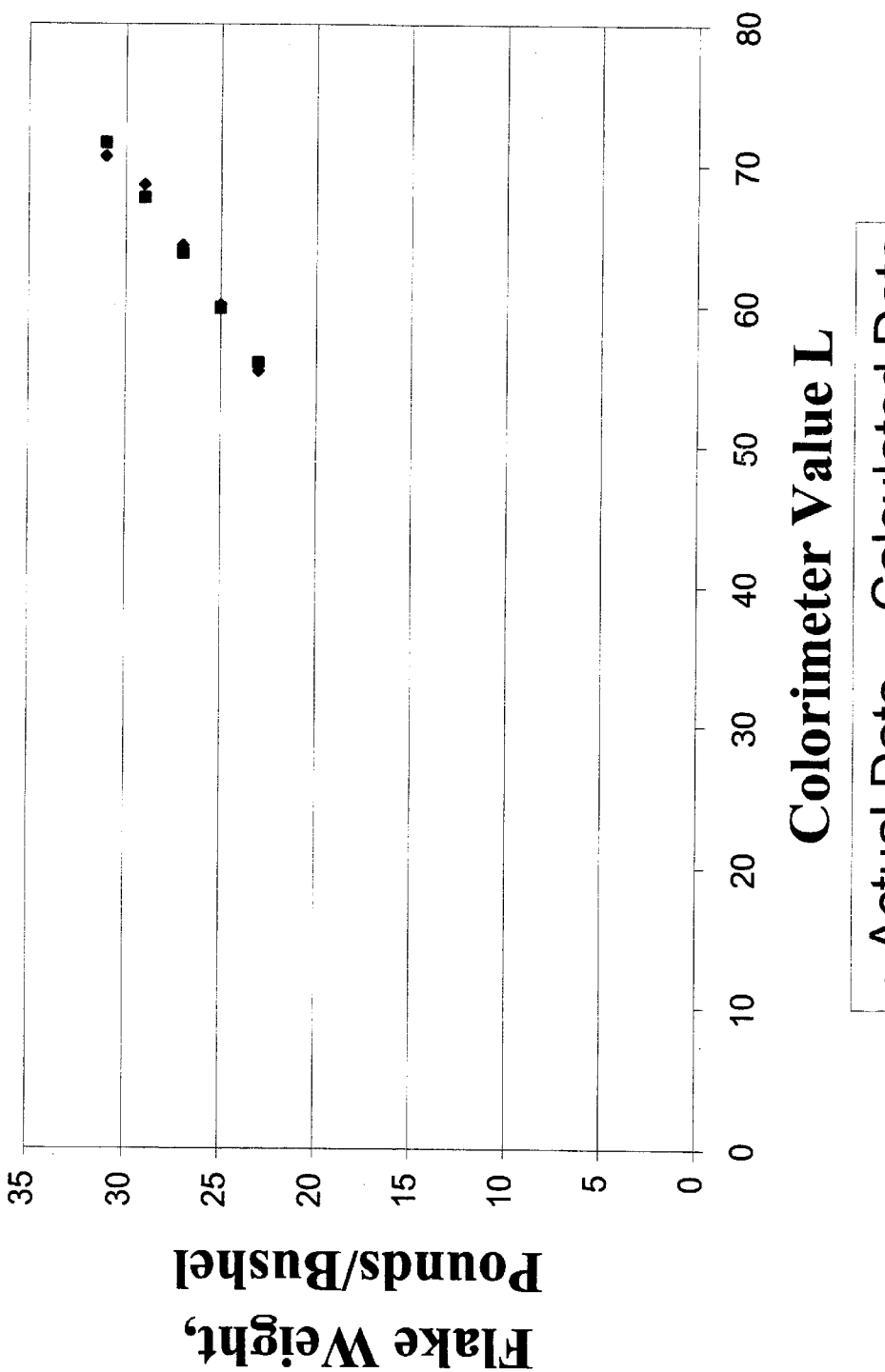
FIG. 4 graphically depicts the actual data points recited in FIG. 3 along with calculated values using parameters derived from a first order regression analysis of the data recited in FIG. 3.

FIG. 3 graphically depicts the observed colorimeter value L* for each flake weight sample. A nearly linear relationship is clearly apparent. Using the mathematical relationship for a linear relationship, namely $$y=mx+b$$

where y equals the flake weight, x equals the colorimeter value L*, m is the slope of a straight line curve, and b equals the y axis intercept, a linear regression analysis of the data in FIG. 3 yields a value of 1.945 for m and a value of 11.185 for the intercept. Turing to FIG. 4, the diamond points depict the actual data observed for calorimeter value L* for each flake weight, and the square points represent calculated data points based on the above-described slope and intercept values. As is readily apparent, the calculated points are nearly identical to the observed points.

Figure 5:
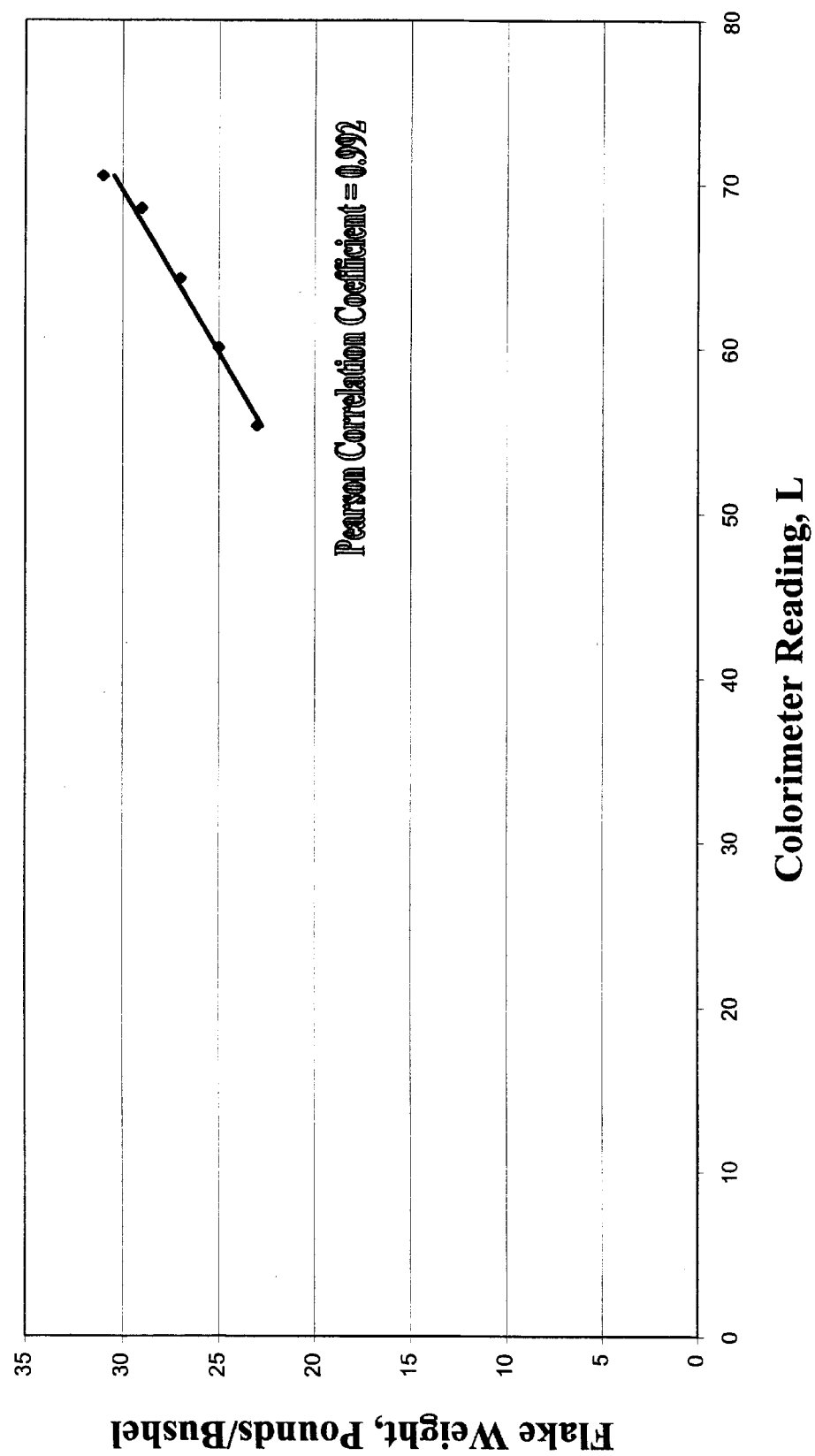
FIG. 5 shows the Pearson Correlation Coefficient for a best-fit, straight line curve fitting the data points recited in FIG. 3.

Turning to FIG. 5, the calculated curve is shown along with the actual data points. The calculated data points have a Pearson Correlation Coefficient of 0.992, and an $R^2$ value of 0.98. Those skilled in the art will readily appreciate that Applicants' optical method using measured color characteristics to monitor the flake weight during and/or after processing of starch-containing materials is highly accurate, cost efficient, and convenient.

Applicants' optical method also allows accurate estimation of the starch availability of a starch-containing material during and/or after processing. Table III recites the laboratory-determined starch availability, and the corresponding colorimeter Lightness Value L*, for each sample obtained.

TABLE III

| Starch Availability | Lightness Value L* |
|---|---|
| 70.6 | 55.3 |
| 71.0 | 60.0 |
| 62.7 | 64.2 |
| 55.6 | 68.5 |
| 57.7 | 70.5 |

Figure 6:
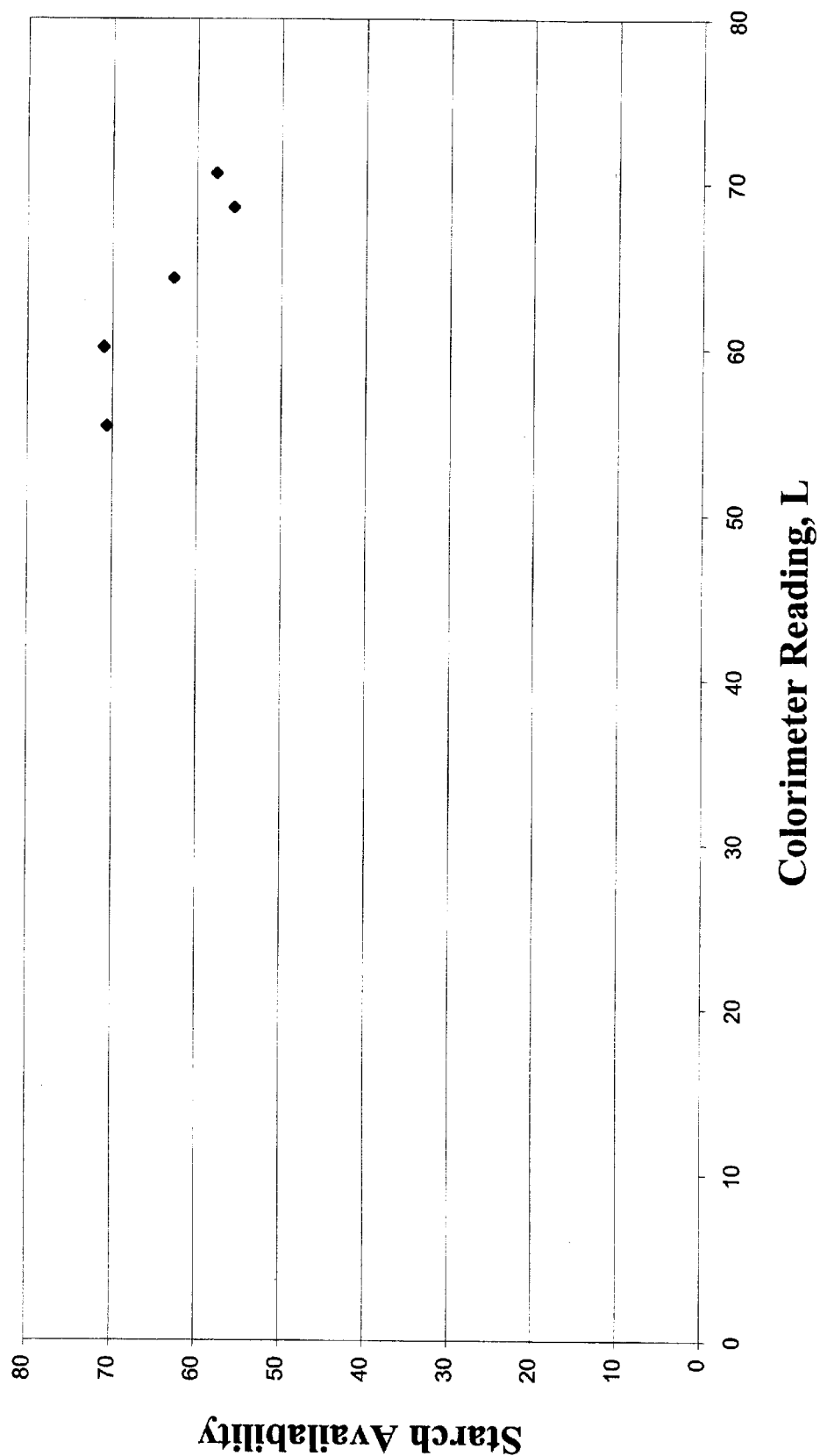
FIG. 6 graphically depicts the relationship between starch availability data obtained by laboratory analyses, and colorimetric data obtained using Applicants' optical method, of five (5) test samples obtained at differing times during the steam processing of corn-based materials.
Figure 7:
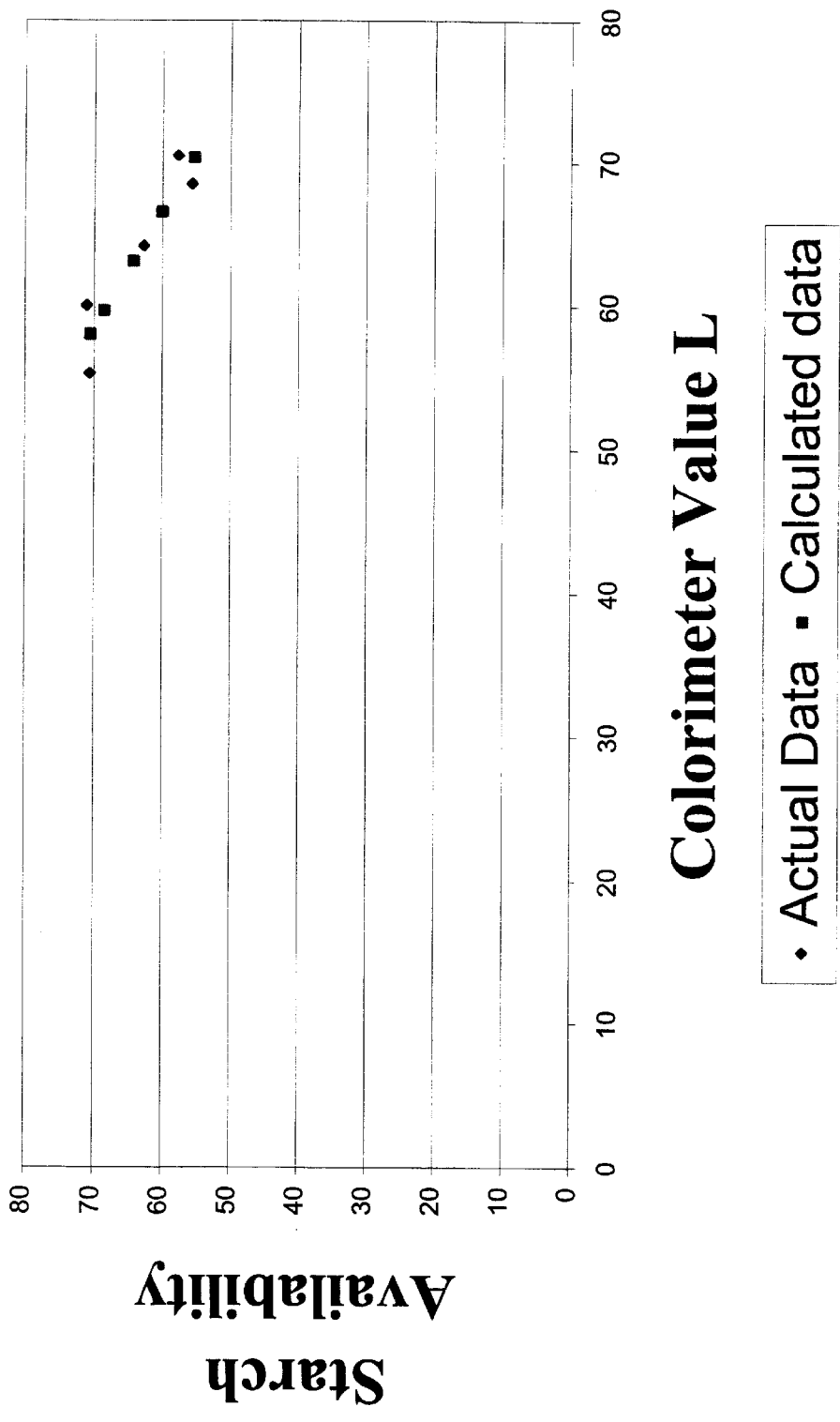
FIG. 7 graphically depicts the actual data points recited in FIG. 6 along with calculated values using parameters derived from a first order regression analysis of the data recited in FIG. 6.

Turning to FIG. 6, the data recited in Table III is graphically depicted. An inverse and linear relationship exists between the starch availability and colorimeter value L*. Again using a first order regression analysis, values for the slope m and intercept b of a straight line curve fitting the data points were determined to be −0.812 and 115.28, respectively. FIG. 7 shows the actual starch availability/colorimeter value L* data as diamond points, and the calculated values using the above-recited values for m and b as square points.

Figure 8:
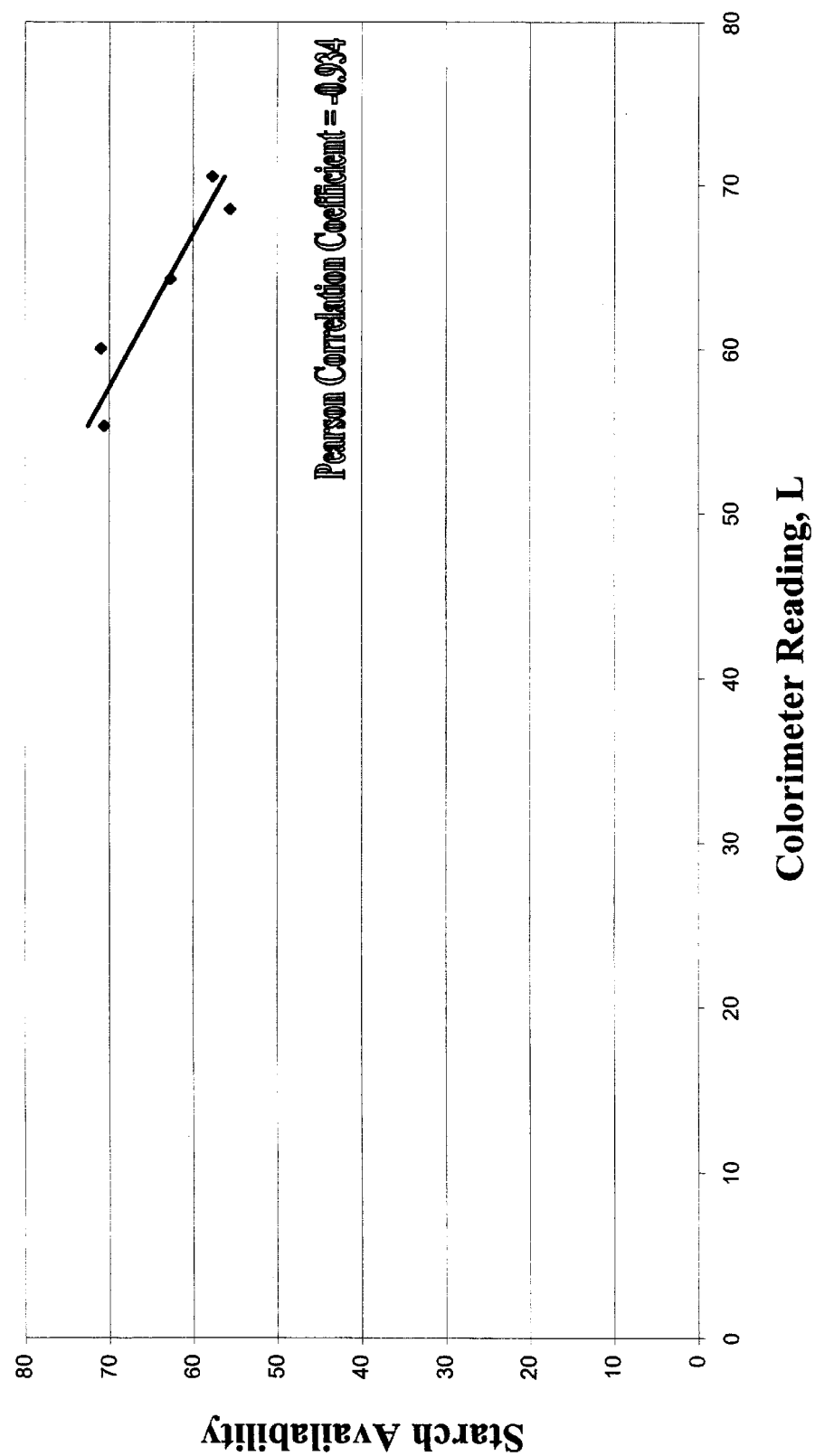
FIG. 8 shows the Pearson Correlation Coefficient for a best-fit, straight line curve using the data points recited in FIG. 6.

As those skilled in the art will appreciate, a good fit can be seen between the experimental data and the calculated data. As shown in FIG. 8, a Pearson Correlation Coefficient of −0.934 and an $R^2$ value of 0.872 were observed. Thus, Applicants' optical method provides an accurate, low cost, and convenient method to determine the starch availability of a starch-containing material during and/or after the process of starch gelatinization.

In addition to the use of Applicants' method to monitor the starch availability of a material during wet processing, i.e. steam flaking, as described above, Applicants have also found that their optical method can be used to determine the degree of processing of a starch-containing material during dry processing. Such dry processing methods include grinding, cracking, rolling, etc. Currently the most common measure of degree of dry processing (grinding, cracking, rolling, etc.) is by sieving and measuring the weight of the different fractions of ground grain retained on the different sieves.

In the wet processing embodiment discussed above, Applicant's method measured optical properties related to starch gelatinization. In this dry processing embodiment, however, the measured optical properties do not correlate with starch gelatinization. Rather, the measured optical properties relate to changes in the proportion of ungelatinized starch to the pigment-containing outer layers, i.e. the yellow outer layer of corn.

In one embodiment of Applicants' method used in conjunction with dry processing, a colorimeter is used to measure color differences during or after processing. Ungelatinized starch is white in color. As the degree of processing (fineness of grind) is increased, the proportion of ungelatinized starch increases, making the sample take on a lighter/whiter appearance. A whiter color correlates with increased processing. Thus, Applicants' optical method can be used with dry processing of a starch-containing material to determine the degree of processing.

Figure 9:
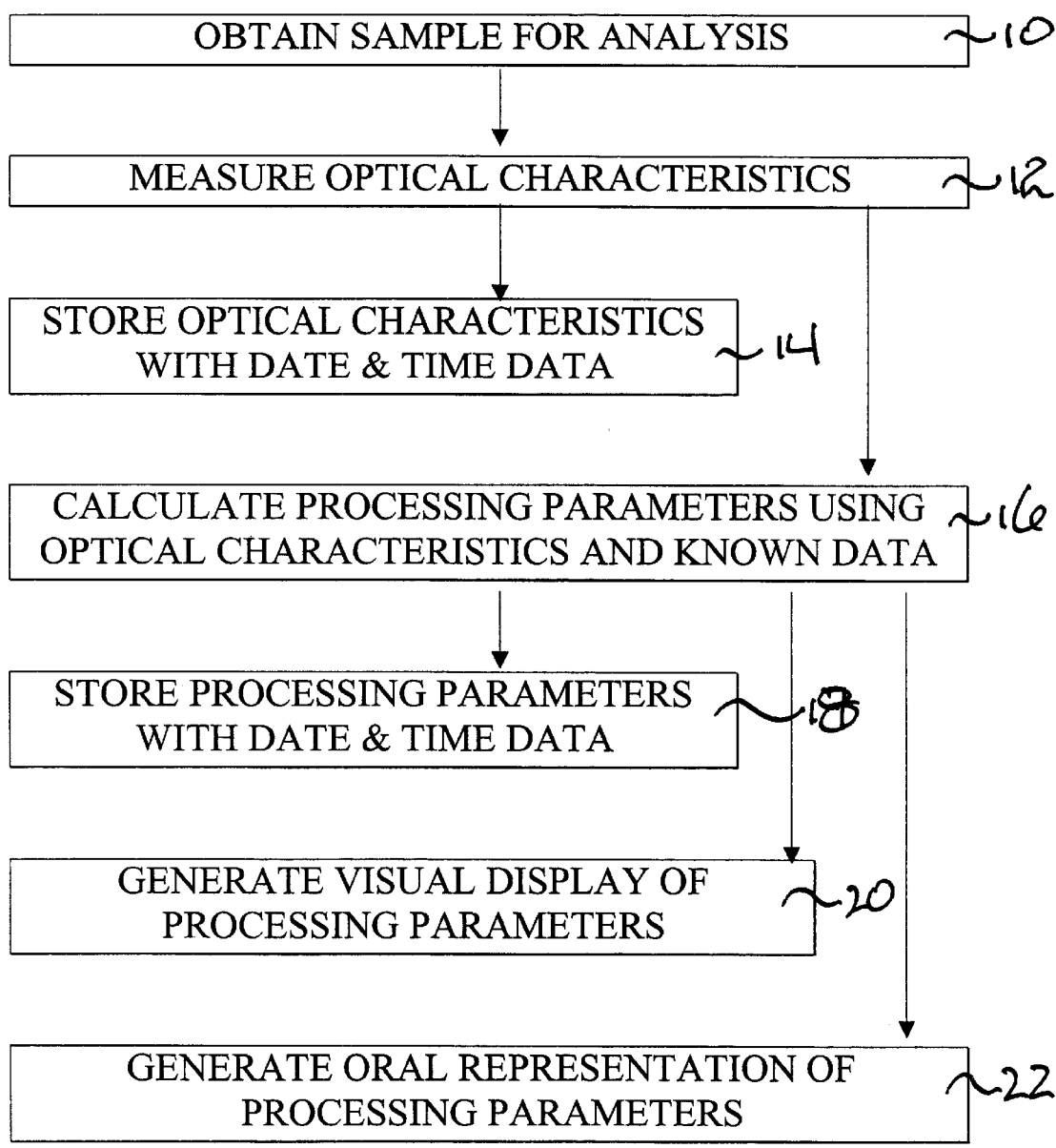
FIG. 9 is a flow chart summarizing Applicants' optical method.

FIG. 9 is a flow chart reciting the steps of Applicants' optical method to measure certain first information during the processing of a starch-containing material. This first information includes optical characteristics such as L, a, b or a combination thereof; the tristimulus values (X, Y, and Z); the CIEL*a*b* color space parameters; hue/lightness/saturation parameters; gloss translucency; fluorescence; and surface texture.

In Step 10 a sample of the material being processed is obtained either during or after processing. In Step 12, the optical characteristics recited above of that test sample are measured by analyzing light reflected from the test sample.

In one embodiment of Applicants' method shown as Step 14, the first information obtained is recorded along with date and time data. Such recordation may be performed manually on a process worksheet. In the alternative, this first information may be stored in a computer database using a stand-alone or networked computer system. As those skilled in the art will appreciate, such a networked computer system may comprise include one or more personal computers and/or one or more mainframe computers.

The first information obtained can then used to accurately estimate second information, such as the flake weight and the starch availability of the processed material. In one embodiment of Applicants' method shown as Step 18, this second information is recorded along with date and time data. Such recordation may be performed manually on a process worksheet. In the alternative, second information may be stored in a computer database using a stand-alone or networked computer system. As those skilled in the art will appreciate, such a networked computer system may comprise include one or more personal computers and/or one or more mainframe computers.

In another embodiment shown as Step 20, the second information is visually displayed on a display device such as a computer monitor. The display device may be located nearby the equipment used to measure the optical characteristics of the test sample, and/or the display device may be located near the work station used to process the starch-containing material.

As shown in Step 22, Applicants' method may optionally generate an oral representation of the second information. This auditory representation may be announced using a device located nearby the equipment used to measure the optical characteristics of the processed material, and/or using a device located near the processing equipment and in view of the manufacturing personnel running the process.

While the invention has been described in detail herein in accordance with certain preferred embodiments thereof, many modifications and changes therein may be effected by those skilled in the art. Accordingly, it is intended by the appended claims to cover all such modifications and changes as fall within the true spirit and scope of the invention.

We claim:

1. A method to monitor the processing of a starch-containing material, comprising the steps of:

heating a starch-containing material;

obtaining (N) samples of said starch-containing material;

determining (N) L* values, wherein the (i)th sample has the (i)th L*value, wherein (i) is an integer greater than or equal to 1 and less than or equal to (N), wherein said (N) L* values comprise lightness coordinates in the Commission Internationale de l'Eclairage L*a*b* color space;

determining (N) starch availability values, wherein the (i)th sample has the (i)th starch availability value; and correlating said (N) L* values with said (N) starch availability values.

2. The method of claim 1, wherein (N) is 5.

3. The method of claim 1, further comprising the steps of:

determining a calibration curve using said (N) L* values and said (N) flake weight values;

processing said starch-containing material;

obtaining a processing sample of said starch-containing material during processing;

determining the L* value for said processing sample; and determining the starch availability value for said processing sample.

4. The method of claim 3, wherein said processing is selected from the group consisting of grinding, dry rolling, steam rolling, pelletizing, steam flaking, pressure flaking, popping, micronizing, exploding, extruding, roasting, high moisture harvesting, reconstitution, and combinations thereof.

5. The method of claim 1, wherein said starch-containing material is selected from the group consisting of corn, wheat, oats, rice, tapioca, potatoes, milo, sorghum, and mixtures thereof.

6. A method to monitor the processing of a starch-containing material, comprising the steps of:

forming a starch-containing material into flakes;

obtaining (N) samples of said starch-containing material;

determining (N) flake weight values, wherein the (i)th sample has the (i)th flake weight, wherein (i) is between 1 and (N);

determining (N) L* values, wherein the (i)th sample has the (i)th L* value, and wherein said (N) L* values comprise lightness coordinates in the Commission Internationale de l'Eclairage L*a*b* color space for said (N) samples;

correlating said (N) L* values and said (N) flake weight values.

7. The method of claim 1, wherein (N) is 5.

8. The method of claim 1, further comprising the steps of:

determining a calibration curve using said (N) L* values and said (N) flake weight values;

processing said starch-containing material;

obtaining a processing sample of said starch-containing material during processing;

determining the L* value for said processing sample; and determining the flake weight for said processing sample.

9. The method of claim 8, wherein said processing is selected from the group consisting of grinding, dry rolling, steam rolling, pelletizing, steam flaking, pressure flaking, popping, micronizing, exploding, extruding, roasting, high moisture harvesting, reconstitution, and combinations thereof.

10. The method of claim 6, wherein said starch-containing material is selected from the group consisting of corn, wheat, oats, rice, tapioca, potatoes, milo, sorghum, and mixtures thereof.

* * * * *